United States Patent
Schneider et al.

(10) Patent No.: US 6,429,227 B1
(45) Date of Patent: Aug. 6, 2002

(54) HYDROXYEICOSATETRAENOATE SALTS, COMPOSITIONS AND METHODS OF USE IN TREATING DRY EYE DISORDERS

(75) Inventors: L. Wayne Schneider; Raymond E. Conrow, both of Crowley; Daniel A. Gamache; Terri Pasquine, both of Arlington; John M. Yanni, Burleson; Haresh G. Bhagat, Fort Worth, all of TX (US)

(73) Assignee: Alcon Universal Ltd., Hunenberg (CH)

( * ) Notice: Subject to any disclaimer, the term of this patent is extended or adjusted under 35 U.S.C. 154(b) by 1 days.

(21) Appl. No.: 09/694,615

(22) Filed: Oct. 23, 2000

Related U.S. Application Data

(60) Provisional application No. 60/164,382, filed on Nov. 9, 1999, provisional application No. 60/164,384, filed on Nov. 9, 1999, and provisional application No. 60/164,370, filed on Nov. 9, 1999.

(51) Int. Cl.$^7$ ............................................. A61K 31/215
(52) U.S. Cl. ...................... 514/530; 514/552; 514/573; 514/912
(58) Field of Search ................................ 514/530, 552, 514/573, 912

(56) References Cited

U.S. PATENT DOCUMENTS

| | | | |
|---|---|---|---|
| 3,991,759 A | 11/1976 | Urquhart | 128/260 |
| 4,131,651 A | 12/1978 | Shah et al. | 424/78 |
| 4,370,325 A | 1/1983 | Packman | 424/245 |
| 4,409,205 A | 10/1983 | Shively | 424/78 |
| 4,421,748 A | 12/1983 | Trager et al. | 424/199 |
| 4,744,980 A | 5/1988 | Holly | 424/78 |
| 4,753,945 A | 6/1988 | Gilbard et al. | 514/263 |
| 4,818,537 A | 4/1989 | Guo | 424/427 |
| 4,868,154 A | 9/1989 | Gilbard et al. | 514/13 |
| 4,883,658 A | 11/1989 | Holly | 424/80 |
| 4,906,467 A | 3/1990 | Schwartzman et al. | 424/80 |
| 4,914,088 A | 4/1990 | Glonek et al. | 514/76 |
| 4,921,644 A | 5/1990 | Lau et al. | 264/4.1 |
| 4,923,700 A | 5/1990 | Kaufman | 424/427 |
| 4,966,773 A | 10/1990 | Gressel et al. | 424/489 |
| 5,041,434 A | 8/1991 | Lubkin | 514/182 |
| 5,064,655 A | 11/1991 | Uster et al. | 424/450 |
| 5,075,104 A | 12/1991 | Gressel et al. | 424/78.04 |
| 5,174,988 A | 12/1992 | Mautone et al. | 424/45 |
| 5,278,151 A | 1/1994 | Korb et al. | 514/76 |
| 5,290,572 A | 3/1994 | MacKeen | 424/602 |
| 5,294,607 A | 3/1994 | Glonek et al. | 514/76 |
| 5,306,483 A | 4/1994 | Mautone | 424/45 |
| 5,358,706 A | 10/1994 | Marlin et al. | 424/78.04 |
| 5,371,108 A | 12/1994 | Korb et al. | 514/762 |
| 5,389,383 A | 2/1995 | Huth | 424/650 |
| 5,403,598 A | 4/1995 | Beck et al. | 424/717 |
| 5,403,841 A | 4/1995 | Lang et al. | 514/226.8 |
| 5,455,265 A | 10/1995 | Chandraratna | 514/448 |
| 5,578,586 A | 11/1996 | Glonek et al. | 514/76 |
| 5,620,921 A | 4/1997 | Sullivan | 514/178 |
| 5,696,166 A | 12/1997 | Yanni et al. | 514/573 |
| 5,800,807 A | 9/1998 | Hu et al. | 424/78.04 |
| 6,281,192 B1 | 8/2001 | Leahy et al. | 514/8 |

FOREIGN PATENT DOCUMENTS

| | | |
|---|---|---|
| CA | 1 251 736 | 3/1989 |
| EP | 0 097 059 A2 | 12/1983 |
| EP | 0 132 089 A1 | 1/1985 |
| WO | WO 91/12808 | 9/1991 |
| WO | WO 92/04905 | 4/1992 |
| WO | WO 98/16240 | 4/1998 |

OTHER PUBLICATIONS

Alpert et al., "Human Tracheal Epithelial Cells Selectively Incorporate 15–Hydroxyeicosatetraenoic Acid into Phosphatidylinositol," *Am. J. Respir. Cell Mol. Biol.*, vol. 8, pp. 273–281 (1993).

Corey et al., 12–Hydroxy–5.8.15–(Z)–10–(E)–Eicosatetraenoic Acid (12–HETE). *The Logic of Chemical Synthesis*, John Wiley and Sons, sections 12.9 and 12.11 (1989).

Corfield et al., "Ocular Mucins: Purification, Metabolism and Functions," *Prog Retinal Eye Res.*, vol. 16, pp. 627–656 (1997).

Danjo et al., "Alternation of Mucin in Human Conjunctival Epithelia in Dry Eye," *Invest Ophthalmol Vis. Sci.*, vol. 39; pp. 2602–2609 (1998).

Dartt et. al., Vasoactive intestinal peptide–stimulated glycocongjugate secretion from conjunctival goblet cells. Experimental Eye Research, vol. 63, pp. 27–34, (1996).

Dilly et al., "Surface Changes in the Anesthetic Conjuctiva in Man, with Special Reference to the Production of Mucus from a Non–Goblet–Cell Source," *British Journal of Ophthalmology*, vol. 65; pp. 833–842 (1981).

Dohlman, "Symposium on the Dry Eye, New Concepts in Ocular Xerosis," *Ophthalmological Societies of the United Kingdom*, vol. XCI; pp. 105–118 (1971).

Glasgow et al., "Tear lipocalins bind a broad array of lipid ligands," *Current Eye Research*, vol. 14(5), pp. 363–372 (1995).

Graber et al., 15–Hydroxyeicosatetraenoic Acid Stimulates Migration of Human Retinal Microvessel Endothelium In Vitro and Neovascularization In Vivo, *Prostaglandins*, vol. 39 (6); pp. 665–673 (1990).

Graff et al., Activation of Soluble Splenic Cell Guanylate Cyclase by Prostaglandin Endoperoxides, and Fatty Acid Hydroperoxides, *J. of Bilogical Chemistry*, vol. 253 (21) pp. 7662–7676 (1978).

(List continued on next page.)

*Primary Examiner*—Zohreh Fay
(74) *Attorney, Agent, or Firm*—Patrick M. Ryan

(57) ABSTRACT

HETE salts, the preparation of HETE salts, the preparation of stable and efficacious HETE compositions, HETE compositions and methods of use for treating dry eye are disclosed.

29 Claims, 1 Drawing Sheet

OTHER PUBLICATIONS

Graff et al., "Preparation of 15–L–Hydroperoxy–5.8.11.13–eicosatetraenoic Acid 9215 (HPETE)," *Methods in Enzymology*, vol. 86; pp. 386–392 (1982).

Greiner et al., "Histochemical Analysis of Secretory Vesicles in Non–Goblet Conjunctival Epithelial Cells," *Acta Ophthalmol.*, vol. 63; pp. 89–92 (1985).

Greiner et al., Meibomian gland phospholipids, *Current Eye Research*, vol. 15(4); pp. 371–375 (1996).

Greiner et al., "Mucus Secretory Vesicles in Conjunctival Epithelial Cells of Wearers of Contact Lenses," *Arch Ophthalmol.*, vol. 98; pp. 1843–1846 (1980).

Greiner et al., "Phospholipids in Meibomian Gland Secretion," *Ophthalmic Res.*, vol. 28, pp. 44–49 (1996).

Hamberg et al., "Identification of 15–hydroxy–5.8.11.13–eicosatetraenoic acid (15–HETE) as a major metabolite of arachidonic acid in human lung," *Acta Physiol Scand.*, vol. 110; pp. 219–221 (1980).

Holly et al., "Tear Physiology and Dry Eyes," *Surv. Ophthalmol.*, vol. 22; pp. 69–87 (1977).

Holzfeind et al., "The Human Lacrimal Gland Synthesizes Apolipoprotein D mRNA in Addition to Tear Prealbumin mRNA, Both Species Encoding Members of the Lipocalin Superfamily," *Exp. Eye Res.*, vol. 65, pp. 495–500 (1995).

Hutchinson, "Arachidonate 15–lipoxygenase; characteristics and potential biological significance," *Eicosanoids*, vol. 4, pp. 65–74 (1991).

Inatomi et al., "Human Corneal and Conjunctival Epithelia Express MUC1 Mucin," *Invest Ophthalmol Vis Sci.*, vol. 36; pp. 1818–1827 (1995).

Jansen et al., "Phospholipids Chiral at Phosphorus. Synthesis and Stereospecificity of Phosphorothioate Analogues of Platelet–Activating Factor," *Biochemistry*, vol. 27, pp. 4619–4624 (1988).

Johnson et al., 15–Hydroxyeicosatetraenoic Acid is a Potent Inflammatory Mediator and Agonist of Canine Tracheal Mucus Secretion, from the Hypersensitivity Diseases Research, Lipids Research. The Upjohn Company, Kalamazoo, Michigan, pp. 917–922 (1984).

Kessing et al., "Mucous Gland System of the Conjunctiva," *Acta Ophthalmol. Suppl.*, vol. 95; pp. 1–133 (1968).

Korb et al., Tear Film Lipid Layer Formation: Implications for Contact Lens Wear, *Optometry and Vision Science*, vol. 73(3), pp. 189–192 (1996).

Legrand et al., "Substitution of 15–Hydroxyeicosatetraenoic Acid in the Phosphoinositide Signaling Pathway," *J. of Biological Chemistry*, vol. 266 (12), pp. 7570–7577 (1991).

Lemp et al., "Report of the National Eye Institute/Industry Workshop on Clinical Trials in Dry Eyes," *CLAO*, vol. 21(4), pp. 221–231 (1995).

Lemp, "Tear Substitutes in the Treatment of Dry Eyes," *External Ocular Diseases: Diagnosis and Current Therapy*, Laibson and Trobe (ed.) Little, Brown and Company, Boston; vol. 13(4); pp. 145–153 (1973).

Marom et al., "Effects of Arachidonic Acid, Monohydroxyeicosatetraenoic Acid and Prostaglandins on the Release of Mucous Glycoproteins from Human Airways In Vitro," *The J. of Clinical Investigation*, vol. 67; pp. 1695–1702 (1981).

Marom et al., "Human Airway Monohydroxyeicosatetraenoic Acid Generation and Mucus Release," *Journal of Clinical Investigation*, vol. 72, pp. 122–127 (1983).

Martini et al., "Regiocontrol of Soybean Lipoxygenase Oxygenation. Application to the Chemoenzymatic Synthesis of Methyl 15(S)–HETE and Dimethyl 5(S)–, 15(S)–HETE," *Journal of Organic Chemistry*, vol. 61, pp. 9062–9064 (1996).

Masferrer et al., "12(R)–Hydroxyeicosatetraenoic Acid, An Endogenous corneal Arachidonate Metabolite, Lowers Intraocular Pressure in Rabbits," *Investigative Ophthalmology and Visual Science*, vol. 31(3); pp. 535–539 (1990).

McCulley et al., "Tear Film Structure and Dry Eye," *Contactologia*, vol. 20, pp. 145–149 (1998).

Mysore et al., "Controlled Ocular Drug Delivery and Vesicular Systems: An Overview," *Indian Drugs*, vol. 33(9), pp. 431–442 (1996).

Nakamura et. al., "Gefarnate stimulates secretion of mucin––like glycoproteins by corneal epithelium in vitro and protects corneal epithelium from dessication in vivo," *Experimental Eye Research*, vol. 65, pp. 569–574 (1997).

Ohno, M.; Otsuka, M. Organic Reactions, vol. 37, p. 1 (1989).

Ohyama et al., "Sensitive Densitometry for the Determination of Platelet–activating Factor and Other Phospholipids in Human Tears," *Analyst*, vol. 121, pp. 1943–1947 (1996).

Pleyer et al., "Analysis of Interactions Between the Corneal Epithelium and Liposomes Qualitative and Quantitative Fluorescence Studies of a Corneal Epithelial Cell Line," *Survey of Ophthalmology.*, vol. 39 (Supl. 1), S3–S16 (1995).

Profita et al., "Interleukin–4 Enhances 15–Lipoxygenase Activity and Incorporation of 15(S)–HETE into Cellular Phospholipids in Cultured Pulmonary Epithelial Cells," *Am. J. Respir. Cell Mol. Biol.*, vol. 20, pp. 61–68 (1999).

Prydal et al., "Study of Human Tear Film Thickness and Structure Using Laser Interferometry," *Invest Ophthalmol Vis Sci.*, vol. 33; pp. 2006–2011 (1992).

Shelhamer et al., "The Effects of Archinoids and Leukotrienes on the Release of Mucus from Human Airways," *Chest Supplement*, 24th Aspen Lung Conference, vol. 81(5); pp. 36S–37S (1982).

Shigemitsu et al., "Effects of Mucin Ophthalmic Solution on Epithelial Wound Healing in Rabbit Cornea," *Ophthalmic Res.*, vol. 29; pp. 61–66 (1997).

Shine et al., Keratoconjunctivitis Sicca Associated with Meibomain Secretion Polar Lipid Abnormality, *Arch. Opthalmology*, vol. 116, pp. 849–852 (1998).

Watanabe et al., "Human Corneal and Conjunctival Epithelia Produce a Mucin–like Glycoprotein for the Apical Surface," *Invest Ophthalmol Vis Sci.*, vol. 36; pp. 337–344 (1995).

Wiggins et al., "12(S)–Hydroxy–5.8.10.14–Eicosatetraenoic Acid is a More Potent Neutrophil Chemoattractant Than the 12(R) Epimer in the Rat Cornea," *Prostaglandis*, vol. 49(2) pp. 131–141 (1990).

Yanni et al., "Effect of Intravenously Administered Lipoxygenase Metabolites on Rat Tracheal Mucous Gel Layer Thickness," *Int Arch Allergy Appl Immunol*, vol. 90 pp. 307–309 (1989).

Yu et al., "Effect of Polar Head Groups on the Interactions of Phospholipase $A_2$ with Phosphonate Transition–State Analogues," *Biochemistry*, vol. 32, pp. 10185–10192.

Zhang et al., "Enzymatic Asymmetric Hydroxylation of Pentadienols Using Soybean Lipoxygenase," *J. Am. Chem. Soc.*, vol. 111(26), pp. 9241–9242 (1989).

Zhu et al., Synthesis of Phospholipids Bearing a Conjugated Oxo–polyunsaturated Fatty Acid Residue, *J. Chem. Research* (S)., vol. 8, pp. 500–501 (1999).

HYDROXYEICOSATETRAENOATE SALTS, COMPOSITIONS AND METHODS OF USE IN TREATING DRY EYE DISORDERS

This application claims priority to co-pending U.S. Provisional Applications, U.S. Ser. No. 60/164,382 filed Nov. 9, 1999; U.S. Ser. No. 60/164,384 filed Nov. 9, 1999, and U.S. Ser. No. 60/164,370 filed Nov. 9, 1999.

The present invention is directed to stable hydroxyeicosatetraenoate salt derivatives, compositions containing such salt derivatives and methods of preparation and use in treating dry eye.

BACKGROUND OF THE INVENTION

Dry eye, also known generically as keratoconjunctivitis sicca, is a common ophthalmological disorder affecting millions of Americans each year. The condition is particularly widespread among post-menopausal women due to hormonal changes following the cessation of fertility. Dry eye may afflict an individual with varying severity. In mild cases, a patient may experience burning, a feeling of dryness, and persistent irritation such as is often caused by small bodies lodging between the eyelid and the eye surface. In severe cases, vision may be substantially impaired. Other diseases, such as Sjogren's disease and cicatricial pemphigoid manifest dry eye complications.

Although it appears that dry eye may result from a number of unrelated pathogenic causes, all presentations of the complication share a common effect, that is the breakdown of the pre-ocular tear film, which results in dehydration of the exposed outer surface and many of the symptoms outlined above (Lemp, *Report of the National Eye Institute/Industry Workshop on Clinical Trials in Dry Eyes, The CLAO Journal*, volume 21, number 4, pages 221–231 (1995)).

Practitioners have taken several approaches to the treatment of dry eye. One common approach has been to supplement and stabilize the ocular tear film using so-called artificial tears instilled throughout the day. Other approaches include the use of ocular inserts that provide a tear substitute or stimulation of endogenous tear production.

Examples of the tear substitution approach include the use of buffered, isotonic saline solutions containing water soluble polymers that render the solutions more viscous and thus less easily shed by the eye. Tear reconstitution is also attempted by providing one or more components of the tear film such as phospholipids and oils. Phospholipid compositions have been shown to be useful in treating dry eye; see, e.g., McCulley and Shine, *Tear film structure and dry eye, Contactologia*, volume 20(4), pages 145–49 (1998); and Shine and McCulley, *Keratoconjunctivitis sicca associated with meibomian secretion polar lipid abnormality, Archives of Ophthalmology*, volume 116(7), pages 849–52 (1998). Examples of phospholipid compositions for the treatment of dry eye are disclosed in U.S. Pat. Nos. 4,131,651 (Shah et al.), U.S. Pat. No. 4,370,325 (Packman), U.S. Pat. No. 4,409,205 (Shively), U.S. Pat. Nos. 4,744,980 and 4,883,658 (Holly), U.S. Pat. No. 4,914,088 (Glonek), U.S. Pat. No. 5,075,104 (Gressel et al.), U.S. Pat. No. 5,278,151 (Korb et al.), U.S. Pat. No. 5,294,607 (Glonek et al.), U.S. Pat. No. 5,371,108 (Korb et al.) and U.S. Pat. No. 5,578,586 (Glonek et al.). U.S. Pat. No. 5,174,988 (Mautone et al.) discloses phospholipid drug delivery systems involving phospholipids, propellants and an active substance.

U.S. Pat. No. 3,991,759 (Urquhart) discloses the use of ocular inserts in the treatment of dry eye. Other semi-solid therapy has included the administration of carrageenans (U.S. Pat. No. 5,403,841, Lang) which gel upon contact with naturally occurring tear film.

Another approach involves the provision of lubricating substances in lieu of artificial tears. For example, U.S. Pat. No. 4,818,537 (Guo) discloses the use of a lubricating, liposome-based composition, and U.S. Pat. No. 5,800,807 (Hu et al.) discloses compositions containing glycerin and propylene glycol for treating dry eye.

Aside from the above efforts, which are directed primarily to the alleviation of symptoms associated with dry eye, methods and compositions directed to treatment of the dry eye condition have also been pursued. For example, U.S. Pat. No. 5,041,434 (Lubkin) discloses the use of sex steroids, such as conjugated estrogens, to treat dry eye conditions in post-menopausal women; U.S. Pat. No. 5,290,572 (MacKeen) discloses the use of finely divided calcium ion compositions to stimulate pre-ocular tear film production; and U.S. Pat. No. 4,966,773 (Gressel et al.) discloses the use of microfine particles of one or more retinoids for ocular tissue normalization.

Although these approaches have met with some success, problems in the treatment of dry eye nevertheless remain. The use of tear substitutes, while temporarily effective, generally requires repeated application over the course of a patient's waking hours. It is not uncommon for a patient to have to apply artificial tear solution ten to twenty times over the course of the day. Such an undertaking is not only cumbersome and time consuming, but is also potentially very expensive. Transient symptoms of dry eye associated with refractive surgery have been reported to last in some cases from six weeks to six months or more following surgery.

The use of ocular inserts is also problematic. Aside from cost, they are often unwieldy and uncomfortable. Further, as foreign bodies introduced in the eye, they can be a source of contamination leading to infections. In situations where the insert does not itself produce and deliver a tear film, artificial tears must still be delivered on a regular and frequent basis.

In view of the foregoing, there is a clear need for an effective, convenient treatment for dry eye that is capable of alleviating symptoms, as well as treating the underlying physical and physiological deficiencies of dry eye.

Mucins are proteins which are heavily glycosylated with glucosamine-based moieties. Mucins provide protective and lubricating effects to epithelial cells, especially those of mucosal membranes. Mucins have been shown to be secreted by vesicles and discharged on the surface of the conjunctival epithelium of human eyes (Greiner et al., *Mucous Secretory Vesicles in Conjunctival Epithelial Cells of Wearers of Contact Lenses, Archives of Ophthalmology*, volume 98, pages 1843–1846 (1980); and Dilly et al., *Surface Changes in the Anaesthetic Conjunctiva in Man, with Special Reference to the Production of Mucous from a Non-Goblet-Cell Source, British Journal of Ophthalmology*, volume 65, pages 833–842 (1981)). A number of human-derived mucins which reside in the apical and subapical corneal epithelium have been discovered and cloned (Watanabe et al., *Human Corneal and Conjunctival Epithelia Produce a Mucin-Like Glycoprotein for the Apical Surface, Investigative Ophthalmology and Visual Science*, volume 36, number 2, pages 337–344 (1995)). Recently, Watanabe discovered a new mucin which is secreted via the corneal apical and subapical cells as well as the conjunctival epithelium of the human eye (Watanabe et al., *IOVS*, volume 36, number 2, pages 337–344 (1995)). These mucins provide lubrication, and additionally attract and hold moisture and sebaceous material for lubrication and the corneal refraction of light.

Mucins are also produced and secreted in other parts of the body including lung airway passages, and more specifically from goblet cells interspersed among tracheal/bronchial epithelial cells. Certain arachidonic acid metabolites have been shown to stimulate mucin production in these cells. Yanni reported the increased secretion of mucosal glycoproteins in rat lung by hydroxyeicosatetraenoic acid ("HETE") derivatives (Yanni et al, *Effect of Intravenously Administered Lipoxygenase Metabolites on Rat Tracheal Mucous Gel Layer Thickness, International Archives of Allergy And Applied Immunology*, volume 90, pages 307–309 (1989)). Similarly, Marom has reported the production of mucosal glycoproteins in human lung by HETE derivatives (Marom et al., *Human Airway Monohydroxyeicosatetraenoic Acid Generation and Mucous Release, Journal of Clinical Investigation*, volume 72, pages 122–127 (1983)).

Agents claimed for increasing ocular mucin and/or tear production include vasoactive intestinal polypeptide (Dartt et. al., *Vasoactive intestinal peptide-stimulated glycoconjiugate secretion from conjunctival goblet cells. Experimental Eye Research*, volume 63, pages 27–34, (1996)), gefarnate (Nakmura et. al., *Gefarnate stimulates secretion of mucin-like glycoproteins by corneal epithelium in vitro and protects corneal epithelium from dessication in vivo, Experimental Eve Research*, volume 65, pages 569–574 (1997)), liposomes (U.S. Pat. No. 4,818,537), androgens (U.S. Pat. No. 5,620,921), melanocycte stimulating hormones (U.S. Pat. No. 4,868,154), phosphodiesterase inhibitors (U.S. Pat. No. 4,753,945), and retinoids (U.S. Pat. No. 5,455,265). However, many of these compounds or treatments suffer from a lack of specificity, efficacy and potency and none of these agents have been marketed so far as therapeutically useful products to treat dry eye and related ocular surface diseases.

U.S. Pat. No. 5,696,166 (Yanni et al.) discloses compositions containing HETEs and their derivatives and methods of use for treating dry eye. Yanni et al. discovered that compositions comprising HETEs increase ocular mucin secretion when administered to a patient and are thus useful in treating dry eye. Yanni et al. disclose a genus of HETEs including, without distinction, carboxylate salts. In fact, no examples of carboxylate salts are contained in the Yanni et al. patent. Instead, the only delineated compounds of the disclosed genus are the preferred compounds, 12(S)-HETE-free acid and 15(S)-HETE-free acid. The inventors of the present invention have found that the use of HETE free acids in the preparation of HETE compositions can result in the compositions exhibiting unsuitable shelf-life stability. The inventors of the present invention have unexpectedly discovered that carboxylate salts of HETEs are particularly useful in the preparation of stable HETE compositions, and in methods of treating dry eye. Additionally, while HETE compositions are therapeutically useful in treating an underlying cause of dry eye, such compositions may not immediately alleviate the symptoms of dry eye following administration. In a preferred embodiment of the present invention, compositions providing both immediate and long term dry-eye relief are provided.

SUMMARY OF THE INVENTION

The present invention is directed to stable HETE salts. The present invention is also directed to methods of stabilizing HETE derivatives, compositions containing stabilized HETE derivatives, and the use of these compositions for the treatment of dry eye and other disorders requiring the wetting of the eye, including symptoms of dry eye associated with refractive surgery such as LASIK surgery.

More specifically, the present invention discloses methods of stabilizing HETE derivatives by converting the compounds to their corresponding salts, preparing compositions containing salts of HETE derivatives, and methods of using the compositions for treating dry eye type disorders.

Preferred methods involve the preparation of compositions containing an effective amount of 15(S)-HETE-sodium salt and an effective concentration of ethanol. The compositions are preferably administered topically to the eye.

In a preferred embodiment, salts of HETE derivatives are formulated with an artificial tear component or phospholipid in order to provide compositions that give both immediate and long term relief from dry eye or other disorders requiring the wetting of the eye.

DETAILED DESCRIPTION OF THE INVENTION

Figure 1:
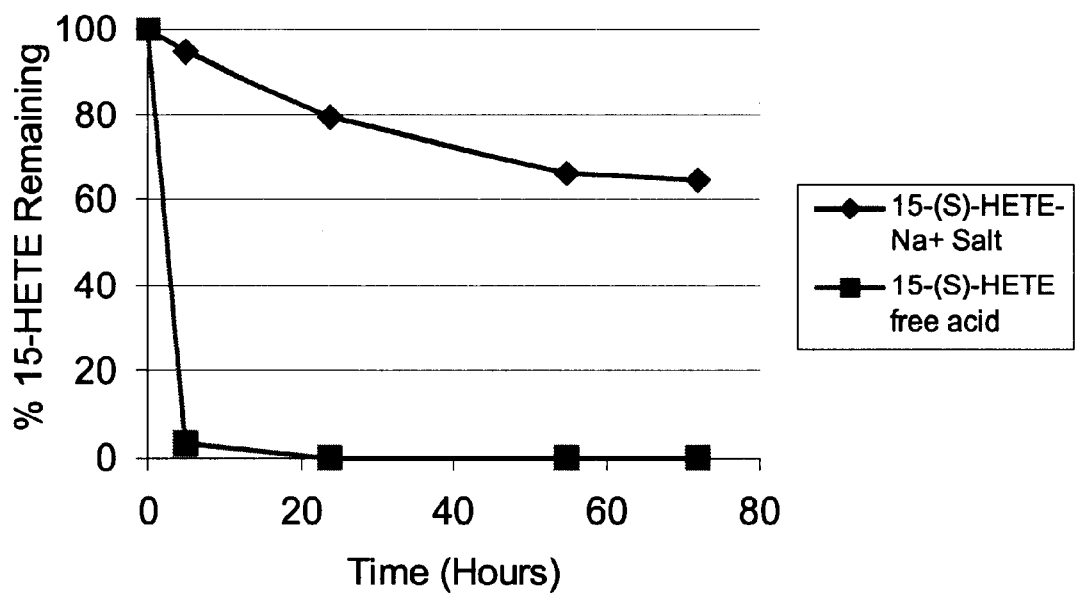
FIG. 1 is a graph illustrating the improved stability of 15(S)-HETE-sodium salt versus 15(S)-HETE free acid.

It has now been discovered that HETE salts are more stable than their corresponding acids, and the use of HETE salts in the preparation of pharmaceutical compositions improves the stability and shelf-life of such compositions. The HETE salt-containing compositions of the present invention are useful for the treatment of dry eye disorders. As used herein, the term "HETE salt" refers to any compound that stimulates ocular mucin production and/or secretion following topical ocular application, and is of the following formulas (I), (II) or (III):

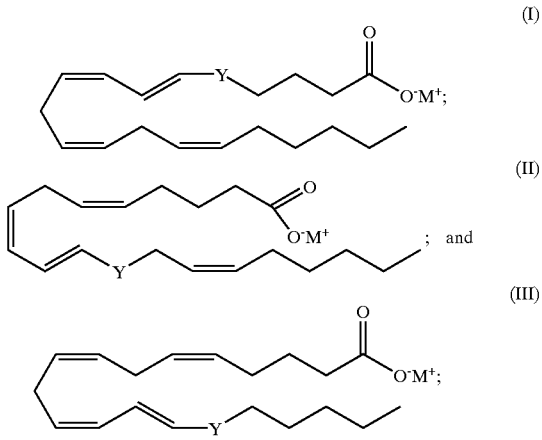

wherein:

$M^+$ is a pharmaceutically acceptable cation selected from the group consisting of: $Na^+$, $K^+$, $Li^+$, $Cs^+$, $(A)_4N^+$, wherein, A is independently H, alkyl, cycloalkyl, (cycloalkyl)alkyl, alkyl(cycloalkyl), aryl, arylalkyl, heteroaryl, or $(A)_4N^+$ forms a heteroaryl, heterocycloalkenyl or heterocycloalkyl ring;

Y is

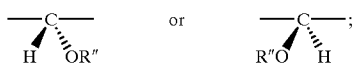

wherein R" is H or OR" is a functionally modified hydroxy group.

As used herein, the terms "pharmaceutically acceptable cation" means any cation (which together with the corresponding carboxylate forms a salt), that would be suitable for therapeutic administration to a patient by any conventional means without significant deleterious health consequences; and "ophthalmically acceptable cation" means any pharmaceutically acceptable cation (which together with the corresponding carboxylate forms a salt) that would be suitable for ophthalmic application, i.e. non-toxic and non-irritating.

The term "free hydroxy group" means an OH. The term "functionally modified hydroxy group" means an OH which has been functionalized to form: an ether, in which an alkyl, aryl, cycloalkyl, heterocycloalkyl, alkenyl, cycloalkenyl, heterocycloalkenyl, alkynyl, or heteroaryl group is substituted for the hydrogen; an ester, in which an acyl group is substituted for the hydrogen; a carbamate, in which an aminocarbonyl group is substituted for the hydrogen; or a carbonate, in which an aryloxy-, heteroaryloxy-, alkoxy-, cycloalkoxy-, heterocycloalkoxy-, alkenyloxy-, cycloalkenyloxy-, heterocycloalkenyloxy-, or alkynyloxycarbonyl group is substituted for the hydrogen. Preferred moieties include OH, OCH$_2$C(O)CH$_3$, OCH$_2$C(O)C$_2$H$_5$, OCH$_3$, OCH$_2$CH$_3$, OC(O)CH$_3$, and OC(O)C$_2$H$_5$.

The term "acyl" represents a group that is linked by a carbon atom that has a double bond to an oxygen atom and a single bond to another carbon atom.

The term "alkyl" includes straight or branched chain aliphatic hydrocarbon groups that are saturated and have 1 to 15 carbon atoms. The alkyl groups may be substituted with other groups, such as halogen, hydroxyl or alkoxy. Preferred straight or branched alkyl groups include methyl, ethyl, propyl, isopropyl, butyl and t-butyl.

The term "cycloalkyl" includes straight or branched chain, saturated or unsaturated aliphatic hydrocarbon groups which connect to form one or more rings, which can be fused or isolated. The rings may be substituted with other groups, such as halogen, hydroxyl, alkoxy, or lower alkyl. Preferred cycloalkyl groups include cyclopropyl, cyclobutyl, cyclopentyl and cyclohexyl.

The term "alkenyl" includes straight or branched chain hydrocarbon groups having 1 to 15 carbon atoms with at least one carbon—carbon double bond. The chain hydrogens may be substituted with other groups, such as halogen. Preferred straight or branched alkenyl groups include, allyl, 1-butenyl, 1-methyl-2-propenyl and 4-pentenyl.

The term "cycloalkenyl" includes straight or branched chain, saturated or unsaturated aliphatic hydrocarbon groups which connect to form one or more non-aromatic rings containing a carbon—carbon double bond, which can be fused or isolated. The rings may be substituted with other groups, such as halogen, hydroxyl, alkoxy, or lower alkyl. Preferred cycloalkenyl groups include cyclopentenyl and cyclohexenyl.

The term "alkoxy" represents an alkyl group attached through an oxygen linkage.

The term "carbonyl group" represents a carbon atom double bonded to an oxygen atom, wherein the carbon atom has two free valencies.

The term "alkoxycarbonyl" represents an alkoxy group bonded from its oxygen atom to the carbon of a carbonyl group, the carbonyl group itself being bonded to another atom through its carbon atom.

The term "aminocarbonyl" represents an amino group bonded from its nitrogen atom to the carbon atom of a carbonyl group, the carbonyl group itself being bonded to another atom through its carbon atom.

The term "lower alkyl" represents alkyl groups containing one to six carbons (C$_1$–C$_6$).

The term "halogen" represents fluoro, chloro, bromo, or iodo.

The term "aryl" refers to carbon-based rings which are aromatic. The rings may be isolated, such as phenyl, or fused, such as naphthyl. The ring hydrogens may be substituted with other groups, such as lower alkyl, or halogen.

The term "heteroaryl" refers to aromatic hydrocarbon rings which contain at least one heteroatom such as O, S, or N in the ring. Heteroaryl rings may be isolated, with 5 to 6 ring atoms, or fused, with 8 to 10 atoms. The heteroaryl ring(s) hydrogens or heteroatoms with open valency may be substituted with other groups, such as lower alkyl or halogen. Examples of heteroaryl groups include imidazole, pyridine, indole, quinoline, furan, thiophene, pyrrole, tetrahydroquinoline, dihydrobenzofuran, and dihydrobenzindole.

The term "heterocycloalkyl" refers to a cycloalkyl ring containing at least one heteroatom, such as N, O, or S, within the ring structure. Examples of heterocycloalkyl rings include tetrahydropyran, pyrrolidine, piperidine, piperazine, tetrahydrothiophene, and morpholine.

The term "heterocycloalkenyl" refers to a cycloalkenyl ring containing at least one heteroatom, such as N, O, or S, within the ring structure. Examples of heterocycloalkenyl rings include dihydropyran, pyrroline, and pyridone.

Included within the scope of the present invention are the individual enantiomers of the formula (I), (II) and (III) compounds, as well as their racemic and non-racemic mixtures. The individual enantiomers can be enantioselectively synthesized from the appropriate enantiomerically pure or enriched starting material by means such as those described below. Alternatively, they may be enantioselectively synthesized from racemic/non-racemic or achiral starting materials. (*Asymmetric Synthesis;* J. D. Morrison and J. W. Scott, Eds.; Academic Press Publishers: New York, 1983–1985, volumes 1–5; *Principles of Asymmetric Synthesis;* R. E. Gawley and J. Aube, Eds.; Elsevier Publishers: Amsterdam, 1996). They may also be isolated from racemic and non-racemic mixtures by a number of known methods, e.g. by purification of a sample by chiral HPLC (*A Practical Guide to Chiral Separations by HPLC;* G. Subramanian, Ed.; VCH Publishers: New York, 1994; *Chiral Separations by HPLC;* A. M. Krstulovic, Ed.; Ellis Horwood Ltd. Publishers, 1989), or by enantioselective hydrolysis of a carboxylic acid ester sample by an enzyme (Ohno, M.; Otsuka, M. *Organic Reactions*, volume 37, page 1 (1989)). Those skilled in the art will appreciate that racemic and non-racemic mixtures may be obtained by several means, including without limitation, nonenantioselective synthesis, partial resolution, or even mixing samples having different enantiomeric ratios. Departures may be made from such details within the scope of the accompanying claims without departing from the principles of the invention and without sacrificing its advantages. Also included within the scope of the present invention are the individual isomers substantially free of their respective enantiomers.

Preferred HETE salts of the present invention are those wherein M$^+$ is selected from the group consisting of Na$^+$, K$^+$, NH$_4$$^+$, benzyltrimethylammonium ion, tetrabutylammonium ion, and phenyltrimethyl ammonium ion. The most preferred compounds of the present invention are:

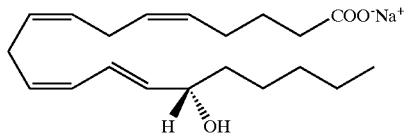

5,8,11,13-Eicosatetraenoic acid, 15-hydroxy-[15S-(5Z,8Z, 11Z,13E)]-sodium salt-("15(S)-HETE-sodium salt"); and

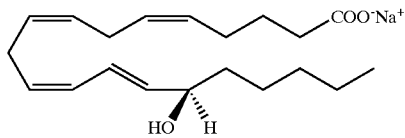

5,8,11,13-Eicosatetraenoic acid, 15-hydroxy-[15R-(5Z,8Z, 11Z,13E)]-sodium salt-("15(R)-HETE-sodium salt").

The HETE salts of the present invention are prepared from the respective HETE free acids (i.e., from compounds of formulas I, II and III, wherein M+ is H).

The HETE free acids are typically derived from arachidonic acid. Certain of the HETE free acids are known in the art and have been isolated ex vivo as well as prepared biosynthetically and synthetically. HETE free acids are made endogenously by the action of lipoxygenases or other enzymes and subsequent reductions through the actions of endogenous peroxidases. Several lipoxygenases are known to exist and are named for the carbon position which they oxidize. Such enzymes include 5-lipoxygenase, 12-lipoxygenase and 15-lipoxygenase. Other enzymes such as cytochrome P-450 have been observed to catalyze the formation of "R-type" HETE oxidized products. Each lipoxygenase catalyzes the addition of a hydroperoxy group at the respective carbon. After hydroperoxidation, which forms such molecules as 5-hydroperoxyeicosatetraenoic acid ("5-HPETE"), 12-HPETE and 15-HPETE, the arachidonate derivatives are reduced to the resulting alcohol by various peroxidases. The resulting molecules include 5-HETE, 12-HETE and 15-HETE free acid.

HETE free acids can be obtained bio-synthetically, by in vitro synthesis. Such methods have involved the use of the respective lipoxygenase, $O_2$, arachidonic acid and a suitable reducing agent (See, Martini et al., *Regiocontrol of Soybean Lipoxygenase Oxygenation. Application to the Chemoenzymatic Synthesis of Methyl 15(S)-HETE and Dimethyl 5(S)-, 15(S)-HETE*. Journal of Organic Chemistry, volume 61, pages 9062–9064 (1996); Graff et al., *Activation of Soluble Splenic Cell Guanylate Cyclase by Prostaglandin Endoperoxides and Fatty Acid Hydroperoxides*, Journal of Biological Chemistry, volume 253, pages 7662–7676 (1978) and Graff, Preparation of 15-*L-Hydroperoxy*-5,8,11,13-*eicosatetraenoic acid* (15-*HPETE*), Methods in Enzymolog, volume 86, pages 386–392 (1982)). HETE free acids may also be synthesized by organic synthetic routes such as described in Corey et al., 12-*Hydroxy*-5,8,14-(*Z*)-10-(*E*)-*eicosatetraenoic Acid* (12-*HETE*), The Logic of Chemical Synthesis, John Wiley and Sons, sections 12.9 and 12.11 (1989). Finally, HETE free acids are commercially available from various sources including Sigma Chemical Co. (St. Louis, Mo.) and Cayman Chemical (Ann Arbor, Mich.). The level of peroxy compounds in the HETE salt raw materials that are used to prepare the pharmaceutical formulations of the present invention may have an impact on the HETE salt's biological activity. Although the precise relationship has not been defined, it is preferable to use HETE salt raw material supplies containing peroxy compounds at levels no greater than about 0.3 ppm. Methods for determining peroxy levels are known in the art (e.g., European Pharmacopoeia 1997 3$^{rd}$ Ed., Method 2.5.5-Peroxide Value).

The HETE salts of the present invention are prepared using the following Scheme 1:

Scheme 1

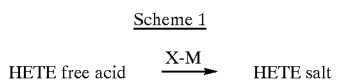

In the above Scheme 1, X-M, which is a base comprised of a positive ion M+, as described above, is added to either the neat HETE free acid, or as dissolved in a solvent, e.g., ethanol. The molar ratio of X-M to HETE free acid will typically range from about 1:1 to 2:1, but is preferably, 1:1. The resultant HETE salt is typically filtered under vacuum and concentrated by rotary evaporation several times and finally dried under high vacuum to yield the neat HETE salt.

EXAMPLE 1

Preparation of 15(S)-HETE-Sodium Salt

To a solution of 8.71 g (27.2 mmol) of 15(S)-HETE acid in 500 mL of absolute ethanol under nitrogen at room temperature was added a solution of 2.28 g (27.2 mmol) of sodium bicarbonate in 60 mL of deionized water. The resulting cloudy mixture was stirred for 1.5 hours until gas evolution had ceased and only faint cloudiness remained, then filtered under vacuum and concentrated by rotary evaporation under vacuum (bath, 24° C.). Absolute ethanol was added to dissolve the residue, and the solution was concentrated as in the previous step. The redissolution/filtration/concentration step was performed twice more. The residue was then dried under vacuum for 16 hours, affording 9.23 g (99%) of the sodium salt of 15(S)-HETE as white powdery solid.

$^{13}$C-NMR (CD$_3$OD): δ 14.39 (CH$_3$), 23.68, 26.27, 26.56, 26.97, 27.33, 28.12, 32.97, 37.67, 38.42 (CH$_2$), 73.30, 126.22, 128.61, 129.22, 129.38, 129.71, 130.59, 130.78, 137.98 (CH), 181.36 (CO$_2$Na).

EXAMPLE 2

Preparation of 15(S)-HETE-Ammonium Salt

Ammonium hydroxide (0.5 mL of a 15 molar aqueous solution) was added to a solution of 0.35 g of 15(S)-HETE in 10 mL of absolute ethanol. The resulting solution was concentrated by rotary evaporation under vacuum. Absolute ethanol (10 mL) was added to the residue and the resulting solution was concentrated by rotary evaporation under vacuum to yield 0.33 g of the ammonium salt of 15(S)-HETE as an oil.

The present invention is also directed to stable, stock compositions comprising one or more HETE salts and ethanol. The inventors have found that storing the HETE salts in an ethanolic solution provides greater stability of the HETE salts over analogous aqueous compositions, or neat HETE salt compositions. Such compositions comprise one or more HETE salts and an amount of ethanol to solubilize the HETE salt in solution. The HETE salt, now dissolved in the ethanolic vehicle is in ionized form. Such resultant compositions are also contemplated by the present invention. Preferably, the ethanolic stock solutions will contain anhydrous ethanol, but aqueous ethanolic solutions are also contemplated hereunder. Generally, the stock solutions will contain ethanol in a concentration of about 25 to 100% volume/volume ("v/v"). Typically, such stock solutions will contain HETE salts in a higher concentration relative to the pharmaceutical compositions of the present invention.

The pharmaceutical compositions of the present invention comprise one or more HETE salts in an amount effective to secrete mucin in the eye and thus eliminate or improve dry eye conditions when administered to the eye. As used herein, the term "pharmaceutically effective amount" refers to an amount of one or more HETE salts which improves the dry eye condition in a mammal. Generally, the HETE salts will be contained in the pharmaceutical compositions in concentrations ranging from about 0.00001 to about 1 percent weight/volume ("% w/v"), and preferably, about 0.00001 to 0.01% w/v. Compositions comprising 15(S)-HETE salt in a concentration of from about 0.00001 to 0.0001% w/v are most preferred.

The HETE salt pharmaceutical compositions will be formulated as solutions, suspensions and other dosage forms for topical administration. Aqueous solutions are generally preferred, based on ease of formulation, biological compatibility (especially in view of the malady to be treated, i.e., dry eye-type disorders), as well as a patient's ability to easily administer such compositions by means of instilling one to two drops of the solutions in the affected eyes. However, the HETE salt pharmaceutical compositions may also be suspensions, viscous or semi-viscous gels, or other types of solid or semi-solid compositions. Suspensions may be preferred for HETE salts which are less soluble in water.

Preferably, the pharmaceutical compositions of the present invention will also contain ethanol. As used herein, "an effective concentration of ethanol" refers to a concentration that enhances the biological efficacy of the HETE salt compositions when dosed topically to the eye. In general, the concentration of ethanol necessary for the enhancement of the HETE salts is believed to be somewhat proportional to the concentration of the HETE salt(s) administered. If a relatively high concentration of HETE salt, e.g., above 0.01% w/v, is administered, the concentration of ethanol in such compositions may be proportionally less than analogous compositions containing lower concentrations of HETE salts. In general, however, the ethanol concentration contained in the compositions of the present invention will range from about 0.001–2% w/v. Compositions containing HETE salt concentrations of about 0.00001–0.01% w/v preferably will contain ethanol in a concentration of about 0.005–0.20% w/v, and most preferably, about 0.02–0.10% w/v.

Preferably, the pharmaceutical compositions of the present invention will also contain one or more surfactant(s). The surfactant(s) may provide additional chemical stabilization of the HETE salts and may further provide for the physical stability of the HETE salts. In other words, the surfactants may aid in preventing chemical degradation of the HETE salts and also prevent the salts from binding to the containers in which their compositions are packaged. Various surfactants useful in topical ophthalmic formulations may be employed. Examples of surfactants include, but are not limited to: Cremophor® EL, polyoxyl 20 ceto stearyl ether, polyoxyl 40 hydrogenated castor oil, polyoxyl 23 lauryl ether and poloxamers, e.g., poloxamer 407. A preferred surfactant is polyoxyl 40 stearate. The amount of surfactant will vary, depending on the amount of HETE salt(s) and the presence of any ethanol included in the formulation. In general, however, the surfactant(s) concentration will be about 0.001 to 2.0% w/v. Preferred pharmaceutical compositions of the present invention will contain about 0.1% w/v of polyoxyl 40 stearate.

The pharmaceutical compositions of the present invention may also include various other ingredients, such as tonicity agents, buffers, preservatives, co-solvents and antioxidants.

Various tonicity agents may be employed to adjust the tonicity of the pharmaceutical composition, preferably to that of natural tears. For example, sodium chloride, potassium chloride, magnesium chloride, calcium chloride and/or mannitol may be added to the composition to approximate physiological tonicity. Such an amount of tonicity agent will vary, depending on the particular agent to be added. In general, however, the compositions will have a tonicity agent concentration of about 0.1–1.5% w/v. Preferred pharmaceutical compositions will contain about 0.75% w/v of sodium chloride.

An appropriate buffer system (e.g., sodium phosphate, sodium acetate, sodium citrate, sodium borate or boric acid) may be added to prevent pH drift under storage conditions. The particular concentration will vary, depending on the agent employed. In general, such a concentration will range from about 0.02 to 2.0% w/v. Preferred compositions will contain about 0.25% w/v of boric acid.

Topical ophthalmic products are typically packaged in multidose form. Preservatives are thus required to prevent microbial contamination during use. Suitable preservatives include: benzalkonium chloride, chlorobutanol, benzododecinium bromide, methyl paraben, propyl paraben, phenylethyl alcohol, edetate disodium, sorbic acid, polyquaternium-1, or other agents known to those skilled in the art. Such preservatives are typically employed at a level of from 0.001 to 1.0% w/v. Unit dose compositions of the present invention will be sterile, but typically unpreserved. Such compositions, therefore, generally will not contain preservatives.

Antioxidants may be added to compositions of the present invention to protect the HETE salts from oxidation during storage. Examples of such antioxidants include, but are not limited to, vitamin E and analogs thereof, ascorbic acid and derivatives, and butylated hydroxyanisole (BHA).

In a preferred embodiment, the pharmaceutical compositions of the present invention include one or more artificial tear or phospholipid components to provide immediate relief while the HETE salts stimulate natural tear production. In this embodiment, the compositions of the present invention provide a two-pronged approach to the treatment of dry eye. The artificial tear or phospholipid component of the compositions provides immediate, temporary relief of dry eye by lubricating and wetting the eye, and the HETE derivative component of the compositions provides pharmaceutical therapy by stimulating the rebuilding of the patient's natural tears through the stimulation of ocular secretion of mucin. An advantage of compositions according to this embodiment, which provide both immediate, temporary relief as well as long-term dry eye relief, is that they do not need to be administered at high frequency typical of non-therapeutic phospholipid compositions. Instead, the compositions of the present invention may be administered as little as one to two times per day to as much as only about eight to ten times a day, depending on the severity of the dry eye condition.

Another advantage of the compositions containing a HETE salt and an artificial tear or phospholipid component is that the compositions provide ease of use over separate, single therapy compositions. In order for a patient to even attempt to gain both short-term and long-term dry eye relief, the patient would need to juggle two separate composition dosing regimens. With such a two composition regimen, the user is encumbered with handling two separate compositions and following the different dosing regimens. Additionally, due to possible overlap of administration, a user of two separate systems may inadvertently overdose one composition or the other, or effectively over-dilute one composition or the other by concomitant dosing of the two compositions. The present invention would solve such problems by providing a single, multi-therapeutic composition for the treatment of dry eye-type diseases and disorders.

As used herein, "one or more artificial tear or phospholipid components" refers to those components that: (i) lubricate, "wet," approximate the consistency of endogenous tears, or otherwise provide temporary relief of the dry eye symptoms and conditions upon ocular administration; (ii) are safe; and (iii) provide an appropriate delivery vehicle for the topical administration of an effective amount of one or more HETE derivatives. As used herein, "an effective amount of one or more artificial tear or phospholipid components" refers to that amount which lubricates, "wets," approximates the consistency of endogenous tears, or otherwise provides temporary relief of the dry eye symptoms and conditions upon ocular administration. In general, the concentration of the artificial tear or phospholipid components in the compositions of the present invention will range from about 0.01 to about 1.0% w/v (phospholipid component) or 2.0% w/v (non-phospholipid component). Preferred amounts will range from about 0.05 to about 0.1% w/v (phospholipid components) and 0.1–0.5% w/v (non-phospholipid component).

The phospholipid components useful in the compositions of the present invention are any natural or synthetic phospholipid compounds comprising a glycerol-phosphoric acid ester or sphingosine backbone. Examples of phospholipids of the present invention are of formula (IV):

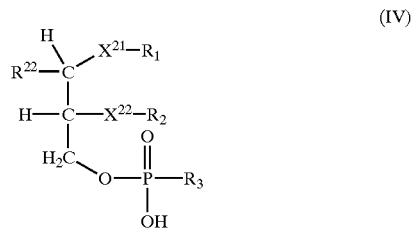

(IV)

wherein, $X^{21}$ and $X^{22}$ are the same or different and are O, NH(C=O), O(C=O), or a direct bond;

$R^{22}$ is H or $CH=CH(CH_2)_{12}CH_3$;

$X_{21}$—$R^1$ is OH, or $R^1$ is $C_{12\text{-}26}$ substituted or unsubstituted alkyl or alkenyl;

$R^2$ is $C_{12\text{-}26}$ substituted or unsubstituted alkyl or alkenyl; and $R^3$ is OH, $OCH_2CH(NH_3^+)COO^-$, $OCH_2CH_2NH_3^+$, $OCH_2CH_2N^+(CH_3)_3$, $OCH_2CH(OH)CH_2OH$ and O-inositol.

The phospholipids may be present as racemic or non-racemic compounds. Preferred phospholipids are those wherein $X^2$—$R^1$ and/or $X^{22}$—$R^2$ comprise fatty acid esters or amides. Natural fatty acids are saturated, monounsaturated or polyunsaturated. Examples of fatty acid residues include, but are not limited to, laurate, myristate, palmitate, palmitoleate, stearate, oleate, linoleate, linolenate, eicosanoate, docosanoate and lignocerate. Preferred phospholipid types are the phosphatidylethanolamines, phosphatidylcholines, phosphatidylserines, phospatidylinositols and sphingomyelins. Examples of specific phospholipids include: 1,2-dipalmitoyl phosphatidyl choline ("DPPC") 1,2-dipalmityl phosphatidyl glycerol ("DPPG"), N-stearyl sphingomyelin, N-palmityl sphingomyelin, N-oleyl sphingomyelin, 1,2-distearoyl phosphatidyl ethanolamine ("DSPE"), 1,2-distearoyl phosphatidyl inositol ("DSPI"), 1-stearoyl-2-palmitoyl phosphatidyl ethanolamine ("SPPE"), 1-stearoyl-2-palmitoyl phosphatidyl choline ("SPPC"), 1,2-dipalmitoyl phosphatidyl ethanolamine ("DPPE"), 1,2-dioleoyl phophatidyl ethanolamine ("DOPE"), 1,2-dioleoyl phophatidyl serine ("DOPS"), and 1,2-dipalmitoyl phosphatidyl serine ("DPPS"). The most preferred phospholipid carriers are the phosphatidylethanolamines and sphingomyelins. Phospholipids are available from a variety of natural sources and may be synthesized by methods known in the art; see, for example, Tsai et. al., *Biochemistry*, volume 27, page 4619 (1988); and Dennis et. al., *Biochemistry*, volume 32, page 10185 (1993).

Various non-phospholipid artificial tear components are known and are useful in providing lubrication, "wetting," approximation of the consistency of endogenous tears, or otherwise providing temporary relief of the dry eye symptoms and conditions upon ocular administration. Such compounds may enhance the viscosity of the composition, and include, but are not limited to: monomeric polyols, such as, glycerol, propylene glycol, ethylene glycol; polymeric polyols, such as, polyethylene glycol, hydroxypropylmethyl cellulose ("HPMC"), carboxy methylcellulose sodium, and hydroxy propylcellulose ("HPC"); hyaluronic acid; chondroitin sulfate; dextrans, such as, dextran 70; water soluble proteins, such as gelatin; and vinyl polymers, such as, polyvinyl alcohol, polyvinylpyrrolidone, povidone and carbomers, such as, carbomer 934P, carbomer 941, carbomer 940, carbomer 974P. In general, the compositions will exhibit a viscosity of 1 to 400 centipoises ("cps"). Preferred compositions will exhibit a viscosity of about 25 cps.

The pharmaceutical compositions of the present invention are intended for administration to a mammal suffering from dry eye or symptoms of dry eye. As such, the compositions of the present invention will be administered topically. In general, the doses used for the above described purposes will vary, but will be in an effective amount to alleviate the symptoms of dry eye, increase mucin production in the eye and thus eliminate or improve dry eye conditions. As used herein, the term "therapeutically effective amount" refers to an amount of compositions of the present invention administered to a patient which improves the dry eye condition of the patient. Generally, 1–2 drops of the pharmaceutical compositions of the present invention will be administered 1–10 times per day for the treatment of dry eye or other ocular disease or disorder. Preferably, 1–2 drops of the compositions will be administered 1–4 times per day.

As used herein, the term "pharmaceutically acceptable carrier" refers to any formulation that is safe, and provides the appropriate delivery for the desired route of administration of an effective amount of at least one HETE salt of the present invention.

The following examples describe compositions of the present invention. Variations of the exemplified compositions may also be prepared, e.g., substituting another HETE salt for 15(S)-HETE-sodium salt and/or modifying the concentration of the HETE salt to between about 0.00001 to 1% w/v, varying the concentrations of the other components present, and modifying the pH (e.g., between about 6–8).

EXAMPLE 3

| Ingredient | Amount (% w/v) |
| --- | --- |
| 15(S)-HETE-sodium salt | 0.000034 |
| Ethanol | 0.0505 |
| Polyoxyl 40 Stearate | 0.1 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s. 100% |

The above composition is prepared by the following method: The batch quantities of polyoxyl 40 stearate, boric acid, sodium chloride, disodium edetate, and polyquaternium-1 are weighed and dissolved by stirring in 90% of the batch quantity of purified water. The pH is adjusted to 7.5±0.1 with NaOH and/or HCl. Under yellow light or reduced lighting, the batch quantity of 15(S)-HETE sodium salt as a stock solution in ethanol and the additional quantity of ethanol necessary for the batch are measured and added. Purified water is added to bring the solution to 100% ("q.s."). The mixture is stirred for five minutes to homogenize and then filtered through a sterilizing filter membrane into a sterile recipient.

Preferably, the above process is performed using glass, plastic or other non-metallic containers or containers lined with such materials.

The formulations of Examples 4 and 5 may be made by a method similar to that described in Example 3.

EXAMPLE 4

| Ingredient | Amount (% w/v) |
| --- | --- |
| 15(S)-HETE-sodium salt | 0.000034 |
| Ethanol | 0.0505 |
| Boric Acid | 0.25 |
| Sodium Chloride | 0.75 |
| Disodium Edetate | 0.01 |
| Polyquaternium-1 | 0.001 |
| NaOH/HCl | q.s., pH = 7.5 |
| Purified Water | q.s 100% |

EXAMPLE 5

| Ingredient | Amount (% w/v) |
| --- | --- |
| 15(S)-HETE-sodium salt | 0.000034 |
| Polyoxyl 40 Stearate | 0.1 |
| Ethanol | 0.0505 |
| Boric Acid | 0.25 |
| Sodium Chloride | 0.75 |
| NaOH/HCl | q.s., pH = 7.5 |
| Purified Water | q.s. 100% |

The following Examples 6–7 illustrate the stability of a HETE salt versus the corresponding HETE free acid.

EXAMPLE 6

15(S)-HETE free acid and 15(S)-HETE-sodium salt were stored under ambient air for four days and exposed to either a temperature of 40° C. in total darkness, or ambient temperature and 300 foot-candles of light (approximately Standard Fluorescent Room Light). Following the four day exposure, aliquots of the samples were analyzed by HPLC for percent remaining HETE and results are reported in Table 1:

TABLE 1

| Sample | Condition | % of Initial Amount Remaining |
| --- | --- | --- |
| 15(S)-HETE-free acid (oil) | Ambient temp., 300 F-C light | 2 |
| 15(S)-HETE-free acid (oil) | 40° C., dark | 0 |
| 15(S)-HETE-sodium salt (solid) | Ambient temp., 300 F-C light | 58 |
| 15(S)-HETE-sodium salt (solid) | 40° C., dark | 86 |

The above data illustrate that the storage of HETEs as free acids results in a high degree of degradation at relatively mild conditions versus the relatively stable storage of the corresponding salts. Thus, this example illustrates the utility of stabilizing HETEs as salts and preparing HETE compositions using HETE salts.

EXAMPLE 7

Ethanolic stock solutions of 15(S)-HETE free acid and 15(S)-HETE free acid with an approximately equimolar amount of sodium hydroxide (to form the sodium salt in situ) were aliquoted to amber glass vials and dried under a stream of helium. The vials were stored at room temperature under ambient atmosphere. At various times, two vials of each were reconstituted with an aliquot of 50/50 acetonitrile/water and assayed by HPLC for 15(S)-HETE. The results are shown in Table 2 and illustrated in FIG. 1:

TABLE 2

| Time (Hours) | 15(S)-HETE-Sodium Salt (% Remaining) | 15(S)-HETE-Free Acid (% Remaining) |
| --- | --- | --- |
| 0 | 100 | 100 |
| 5 | 94 | 4 |
| 24 | 79 | 0 |
| 55 | 66 | 0 |
| 72 | 65 | 0 |

As illustrated above, the sodium salt of 15(S)-HETE is more stable than the corresponding free acid.

The following example illustrates the stabilizing effects of ethanol on the HETE salts of the present invention.

EXAMPLE 8

15(S)-HETE-sodium salt as the neat solid under argon or as solutions in absolute ethanol under ambient atmosphere were stored in amber glass vials in a −20° C. freezer or at room temperature. At various times, the samples were analyzed by HPLC for percent of initial 15(S)-HETE remaining. The results are reported in Table 3:

TABLE 3

| Sample | Condition | Time (Weeks) | | | |
|---|---|---|---|---|---|
| | | 2.0 % of Initial | 4.4 % of Initial | 6.0 % of Initial | 8.4 % of Initial |
| [a]15(S)-HETE-sodium salt (solid) | −20° C. Freezer | 99 | 97 | 95 | 92 |
| [a]15(S)-HETE-sodium salt (solid) | Room Temp. | 72 | 61 | 42 | 28 |
| [b]15(S)-HETE-sodium salt (1 mg/mL in absolute ethanol) | −20° C. Freezer | 102 | 102 | 101 | 101 |
| [b]15(S)-HETE-sodium salt (1 mg/mL in absolute ethanol) | Room Temp. | 101 | 101 | 101 | 101 |
| [b]15(S)-HETE-sodium salt (10 mg/mL in absolute ethanol) | −20° C. Freezer | 101 | 102 | 101 | 101 |
| [b]15(S)-HETE-sodium salt (10 mg/mL in absolute ethanol) | Room Temp. | 101 | 101 | 101 | 100 |

[a]Stored under argon in amber glass vials.
[b]Stored under ambient atmosphere in amber glass vials.

The above data demonstrate that the compositions comprising HETE sodium salts in ethanol were more stable through a variety of conditions than the corresponding neat solids. Thus, this example illustrates the utility of stabilizing HETE salts as solutions in ethanol and preparing HETE salt pharmaceutical compositions using HETE salt stock solutions in ethanol.

The following Examples 9–14 (phospholipid compositions) and 15–23 (non-phospholipid artificial tear component compositions) illustrate specific compositions of the present invention.

EXAMPLE 9

| Ingredient | Amount (% w/v) |
|---|---|
| 15(S)-HETE Sodium Salt | 0.000034 |
| Ethanol | 0.0505 |
| DPPC | 0.05 |
| DPPE | 0.05 |
| Polyoxyl 40 stearate | 0.1 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to ph 6–8 |

The above composition is prepared by the following method. The batch quantities of DPPC, DPPG, sodium chloride, potassium chloride, dibasic sodium phosphate, disodium EDTA, polyquaternium-1, are weighed and dissolved by stirring in 90% of the batch quantity of purified water. The pH is adjusted to 7.5±0.1 with NaOH and/or HCl. Under yellow light or reduced lighting, the batch quantity of 15(S)-HETE sodium salt as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient.

Preferably, the above process is performed using glass, plastic or other non-metallic containers or containers lined with such materials.

The formulations of Examples 10–14 may be made by a method similar to that described in Example 9.

EXAMPLE 10

| Ingredient | Amount (% w/v) |
|---|---|
| 15(S)-HETE Sodium Salt | 0.000034 |
| Ethanol | 0.0505 |
| N-Steatyl Sphingomeylin | 0.1 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

EXAMPLE 11

| Ingredient | Amount (% w/v) |
|---|---|
| HETE derivative | 0.00001–0.01 |
| Ethanol | 0.005–0.20 |
| DPPE | 0.05 |
| DSPE | 1.0 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

EXAMPLE 12

| Ingredient | Amount (% w/v) |
|---|---|
| HETE derivative | 0.00001–0.01 |
| N-oleyl Sphingomyelin | 0.08 |
| DPPE | 0.04 |
| Sodium Chloride | 0.8 |
| Potassium Chloride | 0.12 |
| Dibasic Sodium Phosphate | 0.025 |
| Polyquaternium-1 | 0.001 + 10% excess |
| Purified Water | Qs |
| NaOH/HCl | qs to pH 6–8 |

EXAMPLE 13

| Ingredient | Amount (% w/v) |
|---|---|
| HETE derivative | 0.00001–0.01 |
| DOPS | 0.1 |
| Sodium Chloride | 0.8 |
| Dibasic Sodium Phosphate | 0.025 |
| Disodium EDTA | 0.01 |
| Polyquaternium-1 | 0.001 + 10% excess |
| NaOH/HCl | qs to pH 6–8 |

EXAMPLE 14

| Ingredient | Amount (% w/v) |
|---|---|
| HETE derivative | 0.00001–0.01 |
| N-palmityl Sphingomyelin | 0.1 |
| Sodium Chloride | 0.8 |
| Dibasic Sodium Phosphate | 0.025 |
| Disodium EDTA | 0.01 |
| Polyquaternium-1 | 0.001 + 10% excess |
| NaOH/HCl | qs to pH 6–8 |

EXAMPLE 15

| Ingredient | Amount (% w/v) |
|---|---|
| 15(S)-HETE Sodium Salt | 0.000034 |
| Ethanol | 0.0505 |
| Polyoxyl 40 Stearate | 0.1 |
| HPMC | 0.3 |
| Dextran 70 | 0.1 |
| Benzalkonium Chloride | 0.001 + 10% excess |
| Sodium Chloride | 0.77 |
| Potassium Chloride | 0.12 |
| Disodium EDTA | 0.05 |
| Purified Water | Qs |
| NaOH/HCl | pH 6–8 |

The above composition is prepared by the following method. The batch quantities of HPMC, dextran 70, benzalkonium chloride, sodium chloride, potassium chloride and disodium EDTA are weighed and dissolved by stirring in 90% of the batch quantity of purified water. The pH is adjusted to 7.5±0.1 with NaOH and/or HCl. Under yellow light or reduced lighting, the batch quantity of 15(S)-HETE sodium salt as a stock solution in ethanol and the additional quantity of ethanol necessary for the batch are measured and added. Purified water is added to q.s. to 100%. The mixture is stirred for five minutes to homogenize and then filtered through a sterilizing filter membrane into a sterile recipient.

Preferably, the above process is performed using glass, plastic or other non-metallic containers or containers lined with such materials.

The formulations of Examples 16–23 may be made by a method similar to that described in Example 15.

EXAMPLE 16

| Ingredient | Amount (% w/v) |
|---|---|
| 15(S)-HETE Sodium Salt | 0.000034 |
| Ethanol | 0.0505 |
| Polyoxyl 40 Stearate | 0.1 |
| HPMC | 0.3 |
| Dextran 70 | 0.1 |
| Sodium Chloride | 0.8 |
| Potassium Chloride | 0.12 |
| Dibasic Sodium Phosphate | 0.025 |
| Disodium EDTA | 0.01 |
| Polyquaternium-1 | 0.001 + 10% excess |
| Purified Water | Qs |
| NaOH/HCl | qs to pH 6–8 |

EXAMPLE 17

| Ingredient | Amount (% w/v) |
|---|---|
| 15(S)-HETE Sodium Salt | 0.000034 |
| Ethanol | 0.0505 |
| Polyoxyl 40 Stearate | 0.1 |
| HPMC | 0.3 |
| Dextran 70 | 0.1 |
| Sodium Chloride | 0.52 |
| Potassium Chloride | 0.12 |
| Dibasic Sodium Phosphate | 0.35 |
| Purified Water | Qs |
| NaOH/HCL | qs to pH 6–8 |

EXAMPLE 18

| Ingredient | Amount (% w/v) |
|---|---|
| 15(S)-HETE Sodium Salt | 0.000034 |
| Polyoxyl 40 Stearate | 0.1 |
| HPMC | 0.3 |
| Dextran 70 | 0.1 |
| Sodium Chloride | 0.66 |
| Potassium Chloride | 0.13 |
| Calcium Chloride | 0.0053 |
| Magnesium Chloride | 0.0065 |
| Zinc Chloride | 0.00015 |
| Sodium Bicarbonate | 0.12 |
| Carbon Dioxide/NaOH/HCl | qs to pH 6–8 |
| Purified Water | Qs |

EXAMPLE 19

| Ingredient | Amount (% w/v) |
|---|---|
| 15(S)-HETE Sodium Salt | 0.000034 |
| Ethanol | 0.0505 |
| Polyoxyl 40 Stearate | 0.1 |
| HPMC | 0.3 |
| Dextran 70 | 0.1 |
| Sodium Chloride | 0.66 |
| Potassium Chloride | 0.13 |
| Sodium Bicarbonate | 0.12 |
| Carbon Dioxide/NaOH/HCl | qs to pH 6–8 |
| Purified Water | Qs |

EXAMPLE 20

| Ingredient | Amount (% w/v) |
| --- | --- |
| 15(S)-HETE Sodium Salt | 0.000034 |
| Polyoxyl 40 Stearate | 0.1 |
| Carbomer 934P | 0.3 |
| Mannitol | 4.5 |
| Purified Water | Qs |
| NaOH/HCl | qs to pH 6–8 |

EXAMPLE 21

| Ingredient | Amount (% w/v) |
| --- | --- |
| 15(S)-HETE Sodium Salt | 0.000034 |
| Polyoxyl 40 Stearate | 0.1 |
| Carbomer 934P | 0.3 |
| Mannitol | 4.5 |
| Benzalkonium Chloride | 0.008 + 5% excess |
| Purified Water | Qs |
| NaOH/HCl | qs to pH 6–8 |

EXAMPLE 22

| Ingredient | Amount (% w/v) |
| --- | --- |
| 15(S)-HETE Sodium Salt | 0.000034 |
| HPMC | 0.5 |
| Carbomer 934P | 0.175 |
| Mannitol | 4.5 |
| Purified Water | Qs |
| NaOH/HCl | qs to pH 6–8 |

EXAMPLE 23

| Ingredient | Amount (% w/v) |
| --- | --- |
| 15(S)-HETE Sodium Salt | 0.000034 |
| Ethanol | 0.0505 |
| Polyoxyl 40 Stearate | 0.1 |
| HPMC | 1.0 |
| Dextran 70 | 0.1 |
| Sodium Chloride | 0.66 |
| Potassium Chloride | 0.13 |
| Calcium Chloride | 0.0053 |
| Magnesium Chloride | 0.0065 |
| Zinc Chloride | 0.00015 |
| Sodium Bicarbonate | 0.12 |
| Carbon Dioxide/NaOH/HCl | qs to pH 6–8 |
| Purified Water | Qs |

The invention in its broader aspects is not limited to the specific details shown and described above. Departures may be made from such details within the scope of the accompanying claims without departing from the principles of the invention and without sacrificing its advantages.

What is claimed is:

1. In a pharmaceutical composition for treating dry eye and other disorders requiring the wetting of the eye comprising a HETE derivative according to formulas (I), (II) or (III):

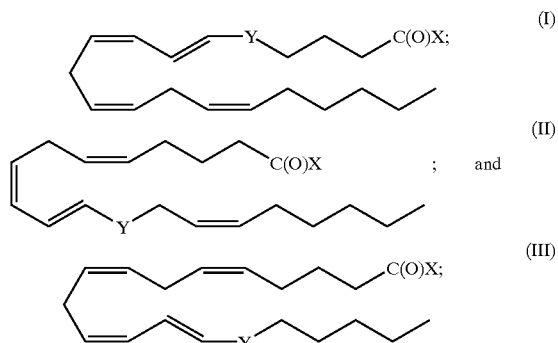

wherein:
X is OR or NHR';
R is H, a cationic pharmaceutically acceptable salt moiety, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy;
R' is H, substituted or unsubstituted alkyl, cycloalkyl, (cycloalkyl)alkyl, aryl, arylalkyl, wherein the substitution is made with a moiety selected from the group consisting of: alkyl, halogen, hydroxy and functionally modified hydroxy; and
Y is

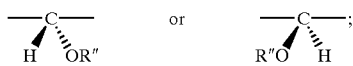

wherein R" is H or C(O)R', the improvement wherein the HETE derivative is an improved stability HETE derivative having
X is OR;
R is a cationic pharmaceutically acceptable salt moiety, such that X is $O^-M^+$;
$M^+$ is a pharmaceutically acceptable cation selected from the group consisting of: $Na^+$, $K^+$, $Li^+$, $Cs^+$, $(A)_4N^+$; and
A is independently H, alkyl, cycloalkyl, (cycloalkyl)alkyl, alkyl(cycloalkyl), aryl, arylalkyl, heteroaryl, or $(A)_4N^+$ together form a heteroaryl, heterocycloalkenyl or heterocycloalkyl ring,
and the composition further comprises ethanol.

2. The composition of claim 1 wherein the HETE derivative is selected from the group consisting of: 5(S)-HETE-sodium salt, 5(R)-HETE-sodium salt, 12(S)-HETE-sodium salt, 12(R)-HETE-sodium salt, 15(S)-HETE-sodium salt, 15(R)-HETE-sodium salt and racemic and non-racemic mixtures thereof.

3. The composition of claim 2 wherein the HETE derivative is 15(S)-HETE-sodium salt.

4. The composition of claim 1 wherein $M^+$ is selected from the group consisting of $Na^+$, $K^+$ and $NH_4^+$.

5. The composition of claim 1 wherein the composition comprises 0.001–2% (w/v) ethanol.

6. The composition of claim 1 further comprising one or more artificial tear or phospholipid components.

7. The composition of claim 6 wherein the composition comprises a phospholipid selected from the group consisting of are selected from the group consisting of phosphatidylethanolamines, phosphatidylcholines, phosphatidylserines, phospatidylinositols and sphingomyelins.

8. The composition of claim 6 wherein the composition comprises a phospholipid of the formula:

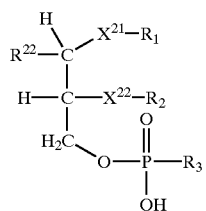

(IV)

wherein, $X^{21}$ and $X^{22}$ are the same or different and are O, NH(C=O), O(C=O), or a direct bond;

$R^{22}$ is H or $CH=CH(CH_2)_{12}CH_3$;

$X^{21}$—$R^1$ is OH, or $R^1$ is $C_{12-26}$ substituted or unsubstituted alkyl or alkenyl;

$R^2$ is $C_{12-26}$ substituted or unsubstituted alkyl or alkenyl; and $R^3$ is OH, $OCH_2CH(NH_3^+)COO^-$, $OCH_2CH_2NH_3^+$, $OCH_2CH_2N^+(CH_3)_3$, $OCH_2CH(OH)CH_2OH$ and O-inositol.

9. The composition of claim 8, wherein the phospholipid is selected from the group consisting of: DPPC, DPPG, DSPI, SPPC, DPPE, DOPS, DSPE, SPPE, DOPE, DPPS, N-stearyl sphingomyelin, N-palmityl sphingomyelin and N-oleyl sphingomyelin.

10. The composition of claim 6 wherein the composition comprises an artificial tear component selected from the group consisting of monomeric polyols; polymeric polyols; hyaluronic acid; chondroitin sulfate; dextrans; water-soluble proteins; and vinyl polymers.

11. The composition of claim 10 wherein the artificial tear component is selected from the group consisting of glycerol; propylene glycol; ethylene glycol; polyethylene glycol; hydroxypropylmethyl cellulose; carboxy methylcellulose sodium; hydroxy propylcellulose; hyaluronic acid; chondroitin sulfate; dextran 70; gelatin; polyvinyl alcohol; polyvinylpyrrolidone; povidone; carbomer 934P; carbomer 941; carbomer 940; and carbomer 974P.

12. The composition of claim 1 wherein the composition further comprises one or more ingredients selected from the group consisting of surfactants, tonicity agents, buffers, preservatives, co-solvents and anti-oxidants.

13. A method for the treatment of dry eye and other disorders requiring the wetting of the eye comprising administering to a mammal a composition comprising ethanol, a pharmaceutically acceptable carrier and a pharmaceutically effective amount of one or more HETE salts according to formulas (I), (II) or (III):

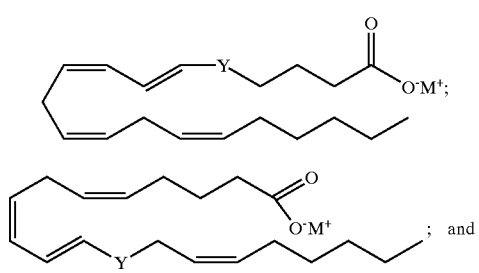

(I)

(II) ; and

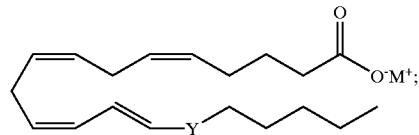

(III)

wherein, $M^+$ is a pharmaceutically acceptable cation selected from the group consisting of: $Na^+$, $K^+$, $Li^+$, $Cs^+$, $(R)_4N^+$, wherein, R is independently H, alkyl, cycloalkyl, (cycloalkyl)alkyl, alkyl(cycloalkyl), aryl, arylalkyl, heteroaryl, or $(R)_4N^+$ together form a heteroaryl, heterocycloalkenyl or heterocycloalkyl ring;

Y is

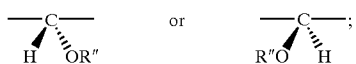

wherein R″ is H or OR″ is a functionally modified hydroxy group.

14. The method of claim 13, wherein the HETE salt is selected from the group consisting of 5(S)-HETE-sodium salt, 5(R)-HETE-sodium salt, 12(S)-HETE-sodium salt, 12(R)-HETE-sodium salt, 15(S)-HETE-sodium salt, 15(R)-HETE-sodium salt and racemic and non-racemic mixtures thereof.

15. The method of claim 14, wherein the HETE salt is 15(S)-HETE-sodium salt.

16. The method of claim 13, wherein $M^+$ is selected from the group consisting of $Na^+$, $K^+$ and $NH_4^+$.

17. The method of claim 13, wherein the composition comprises an amount of ethanol sufficient to enhance the HETE salt's efficacy.

18. The method of claim 13, wherein the amount of ethanol in the composition is 0.001–2% w/v.

19. The method of claim 18, wherein the amount of ethanol in the composition is 0.005–0.20% w/v.

20. The method of claim 15, wherein 15(S)-HETE-sodium salt is contained in the composition in a concentration of between 0.00001–0.01% w/v.

21. The method of claim 20, wherein the composition comprises:

0.00001–0.01% w/v of 15(S)-HETE sodium salt;
0.0505% w/v of ethanol;
0.25% w/v of boric acid;
0.75% w/v of sodium chloride;
0.01% w/v of disodium edetate;
0.001% w/v of polyquaternium-1; and water.

22. The method of claim 21, wherein the composition further comprises polyoxyl 40 stearate in an amount of 0.001 to 2.0% w/v.

23. The method of claim 13, wherein the composition further comprises one or more artificial tear or phospholipid components.

24. The method of claim 23, wherein the composition comprises a phospholipid selected from the group consisting of are selected from the group consisting of phosphatidylethanolamines, phosphatidylcholines, phosphatidylserines, phospatidylinositols and sphingomyelins.

25. The method of claim 23, wherein the composition comprises a phospholipid of the formula:

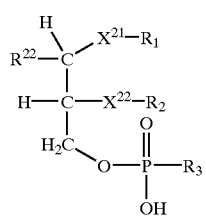

(IV)

wherein, $X^{21}$ and $X^{22}$ are the same or different and are O, NH(C=O), O(C=O), or a direct bond;

$R^{22}$ is H or CH=CH(CH$_2$)$_{12}$CH$_3$;

$X^{21}$—$R^1$ is OH, or $R^1$ is C$_{12-26}$ substituted or substituted alkyl or alkenyl;

$R^2$ is C$_{12-26}$ substituted or unsubstituted alkyl or alkenyl; and $R^3$ is OH, OCH$_2$CH(NH$_3^+$)COO$^-$, OCH$_2$CH$_2$NH$_3^+$, OCH$_2$CH$_2$N$^+$(CH$_3$)$_3$, OCH$_2$CH(OH)CH$_2$OH and O-inositol.

26. The method of claim 25, wherein the phospholipid is selected from the group consisting of: DPPC, DPPG, DSPI, SPPC, DPPE, DOPS, DSPE, SPPE, DOPE, DPPS, N-stearyl sphingomyelin, N-palmityl sphingomyelin and N-oleyl sphingomyelin.

27. The method of claim 23, wherein the composition comprises an artificial tear component selected from the group consisting of monomeric polyols; polymeric polyols; hyaluronic acid; chondroitin sulfate; dextrans; water-soluble proteins; and vinyl polymers.

28. The method of claim 27, wherein the artificial tear component is selected from the group consisting of glycerol; propylene glycol; ethylene glycol; polyethylene glycol; hydroxypropylmethyl cellulose; carboxy methylcellulose sodium; hydroxy propylcellulose; hyaluronic acid; chondroitin sulfate; dextran 70; gelatin; polyvinyl alcohol; polyvinylpyrrolidone; povidone; carbomer 934P; carbomer 941; carbomer 940; and carbomer 974P.

29. The method of claim 13 wherein the dry eye and other disorders requiring wetting of the eye is symptoms of dry eye associated with refractive surgery.

* * * * *